(12) United States Patent
Studer

(10) Patent No.: US 6,269,649 B1
(45) Date of Patent: Aug. 7, 2001

(54) HIGH-PRESSURE FREEZING SYSTEM

(75) Inventor: Daniel Studer, Dotzigen (CH)

(73) Assignee: Leica Mikrosysteme AG, Vienna (AT)

( * ) Notice: Subject to any disclaimer, the term of this patent is extended or adjusted under 35 U.S.C. 154(b) by 0 days.

(21) Appl. No.: 09/588,653

(22) Filed: Jun. 7, 2000

(30) Foreign Application Priority Data

Jul. 6, 1999 (CH) .................................................. 1260/99

(51) Int. Cl.$^7$ ................................ F25B 19/00; F24F 3/16
(52) U.S. Cl. ................................................. 62/51.1; 62/78
(58) Field of Search ................................. 62/51.1, 78, 64, 62/50.1

(56) References Cited

U.S. PATENT DOCUMENTS

| | | | |
|---|---|---|---|
| 4,559,298 | * 12/1985 | Fahy | 435/1 |
| 4,688,387 | * 8/1987 | Conaway | 62/78 |
| 4,745,764 | * 5/1988 | Sitte et al. | 62/78 |
| 5,493,865 | 2/1996 | Wohlwend | 62/51.1 |

FOREIGN PATENT DOCUMENTS

| | | |
|---|---|---|
| 1 806 741 | 6/1969 | (DE) . |
| 87 13 605 | 1/1988 | (DE) . |
| 0 853 238 | 7/1998 | (EP) . |

OTHER PUBLICATIONS

LEICA EM HPF; High Pressure Freezer; 1.K.–LEICA EM HPF–E; Jun. 1994; 2 Sheets.

* cited by examiner

*Primary Examiner*—William Doerrler
(74) *Attorney, Agent, or Firm*—Foley & Lardner

(57) ABSTRACT

The invention relates to a high-pressure freezing system in which the pressure build-up ensues from a prestressed pneumatic cylinder. This results in a particularly rapid pressure rise in the sample holder.

24 Claims, 4 Drawing Sheets

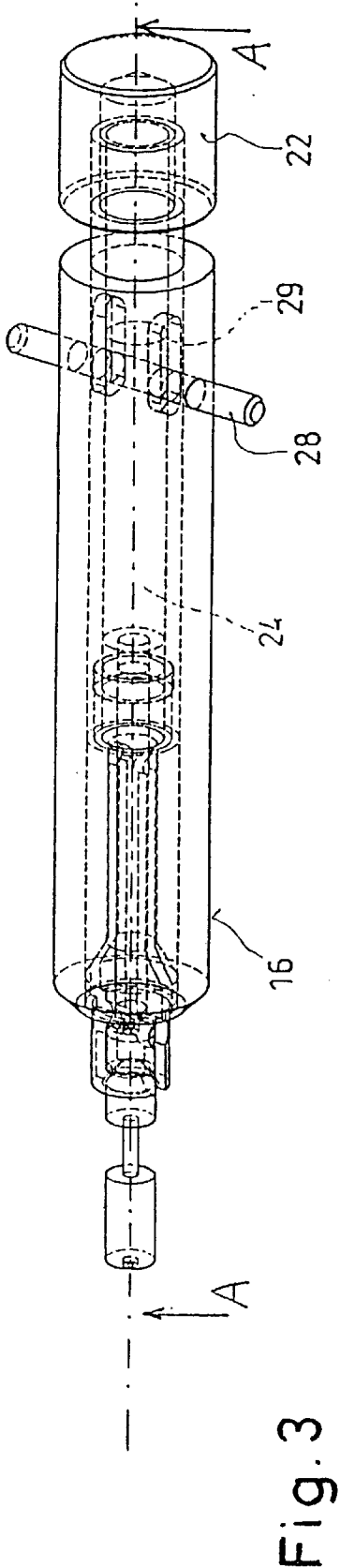
Fig. 3
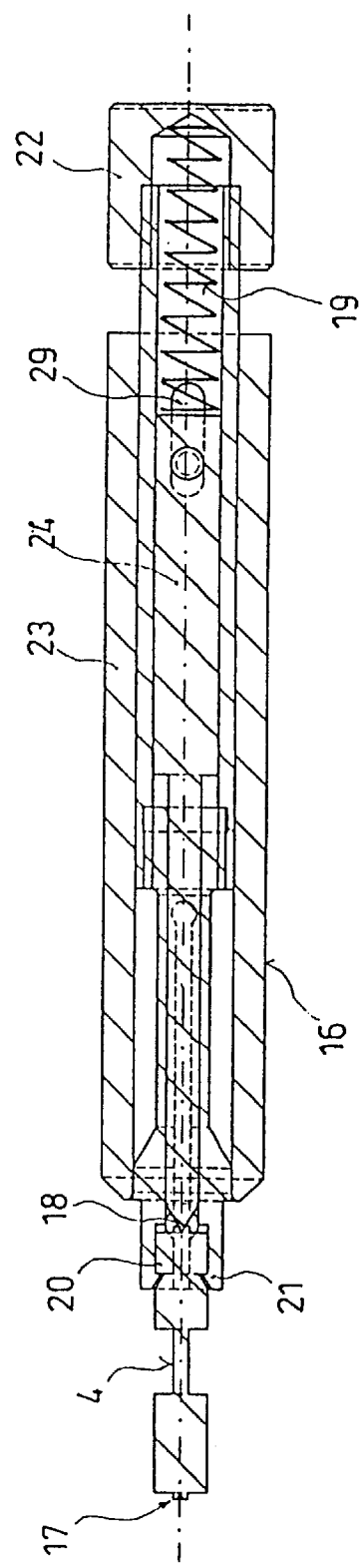
Fig. 4 SCHNITT A-A

HIGH-PRESSURE FREEZING SYSTEM

CROSS REFERENCE TO RELATED APPLICATIONS

This application claims priority of the Swiss Patent Application CH1260/99.

FIELD OF THE INVENTION

The invention relates to a high-pressure freezing system in accordance with the characterizing clause of claim 1. In the sense of the invention, a high-pressure freezing system is understood to be a freezing device for the rapid freezing (vitrification) of aqueous samples under high pressure.

BACKGROUND OF THE INVENTION

Information on the physics of such a freezing process can be found in the German Patent DE-PS-1806741 and the European Patent Application EP-A-0 853238.

In professional circles, for example, such a known system of the applicant is employed, which is successfully marketed under the name "Leica EM HPF"™ and described in the publication "LEICA EM HPF, High Pressure Freezer, 1.K.- LEICA EM HPF-E-6/94, Jun. 1994".

The "Leica EM HPF"™ allows the vitrification of conventional samples under a pressure of ca. 2000 bar at a cooling rate of $10^3$–$10^5$ K/s. For the said appliance, the crucial cooling phase from ambient temperature to –100° C. takes ca. 10 ms (cooling rate $10^4$ K/s) at the surface of the sample. Consequently, all samples with a thickness of ca. 200μm are cooled to –100° C. in ca. 50 ms.

The known cooling technology and the physical processes show clearly: Applying an infinitely high cooling rate to the surface of a biological sample only partially determines the rate of cooling in its centre. A sample of thickness 200 μm, for example, exhibits a cooling rate in its centre of ca. 6000 K/s, regardless of whether an infinite cooling rate is employed at the surface or a cooling rate of ca. 10,000 K/s. The cooling rate is not determined by the pressure. By increasing the pressure, a lower cooling rate is sufficient for vitrification. Therefore, the cooling rate for the vitrification of biological samples is under standard pressure ca. $10^5$–$10^6$ K/s, tinder 2000 bar, however, the cooling rate is only $10^3$–$10^4$ K/s, i.e., it is still possible to vitrify biological samples under high pressure using cooling rates a hundred-fold lower.

The inventor referred in the article "A NEW CONCEPT AND MACHINE FOR HIGH PRESSURE FREEZING" from 15.3.1999, published in the internet under the address "www-mem.unibe.ch/~ danis/abstract HPF", to these and further aspects of high-pressure freezing. He proposed increasing the pressure from 1 bar to 2000 bar within 10 ms by employing a compressed-air cylinder in place of the well-known very bulky and heavy equipment.

Pneumatic cylinders are already employed in a wide variety of applications. Using them to quickly build up high pressures, however, necessitates the use of large and heavy pumps.

SUMMARY OF THE INVENTION

Consequently, the first problem to be solved in the invention is the construction of a high-pressure freezing system, which is lighter than the hitherto known systems but which nevertheless allows a rapid build-up of pressure.

The above problem is solved by the features of independent claim 1 and claim 11 which is a reduction in the constructional size and yet an accelerated pressure build-up.

The dependent claims 2 to 6 and 12 to 18 refer to improved solutions with extensive integration and extensive advantages over the state of the art.

However, the invention is based on a further problem: The aim is a simple pressure adjustment in the range of ca. 1500–2000 bar. The reason for this being that it is known from technical literature that biological samples exposed to pressures exceeding 1600 bar can exhibit irreversible damages. In accordance with the invention, this is possible by merely varying the pneumatic pressure at the prestressed pneumatic cylinder; i.e., altering the input pneumatic pressure at the pneumatic cylinder during the prestressing phase can result in a different driving power at the output end leading to a different or adjustable pressure build-up in the high-pressure cylinder.

In addition, as, in accordance with the invention, pressure build-up and cooling are separated, it is possible to cool the sample using liquid nitrogen to 196° C. In boundary ranges of 200μm, in particular, the cell structure remains undamaged using the procedure of the present invention, which can be allowed for with no difficulty in the selection of the sample dimensions.

During vitrification, very low cooling temperatures, as acquired using liquid and undercooled nitrogen, for example, are of course advantageous, provided that the nitrogen itself —as indicated sporadically in the state of the art —is not exposed to these high pressures. If the undercooled nitrogen were to be used as pressure carrier, this would constitute a potential source of danger at the high pressures and it would not be possible to attain a temperature of –196° C. as the nitrogen is already solid at –196° C. under pressures exceeding 1500 bar.

The dependent claims 7 to 10 and 19 to 24 relate to improvements which can be applied independently to advantage other known high-pressure freezing systems or those still to be designed. This concerns in particular a novel and improved holding device for a sample container in accordance with the European Patent Application EP-A-0 853 238 of the inventor. A new holding device should facilitate the handling of the known sample container and accelerate the changing of sample containers or samples. In particular, this should accelerate the throughput of samples through a vitrification plant and thus achieve an improvement in economic efficiency.

BRIEF DESCRIPTION OF THE DRAWINGS

The subject matter of the invention is described with reference to the embodiments shown in the drawings:

FIG. 3 discloses an oblique view of a new type of arm log holder for a sample container;

FIG. 4 discloses a sectional view of the arm log holder of FIG. 3 and

FIG. 1 shows a symbolic drawing of the arrangement in accordance with the invention. A high-pressure freezing system is used to attain an amorphous state during rapid freezing of aqueous samples, in particular biological samples 33.

DETAILED DESCRIPTION OF THE INVENTION

Figure 1:
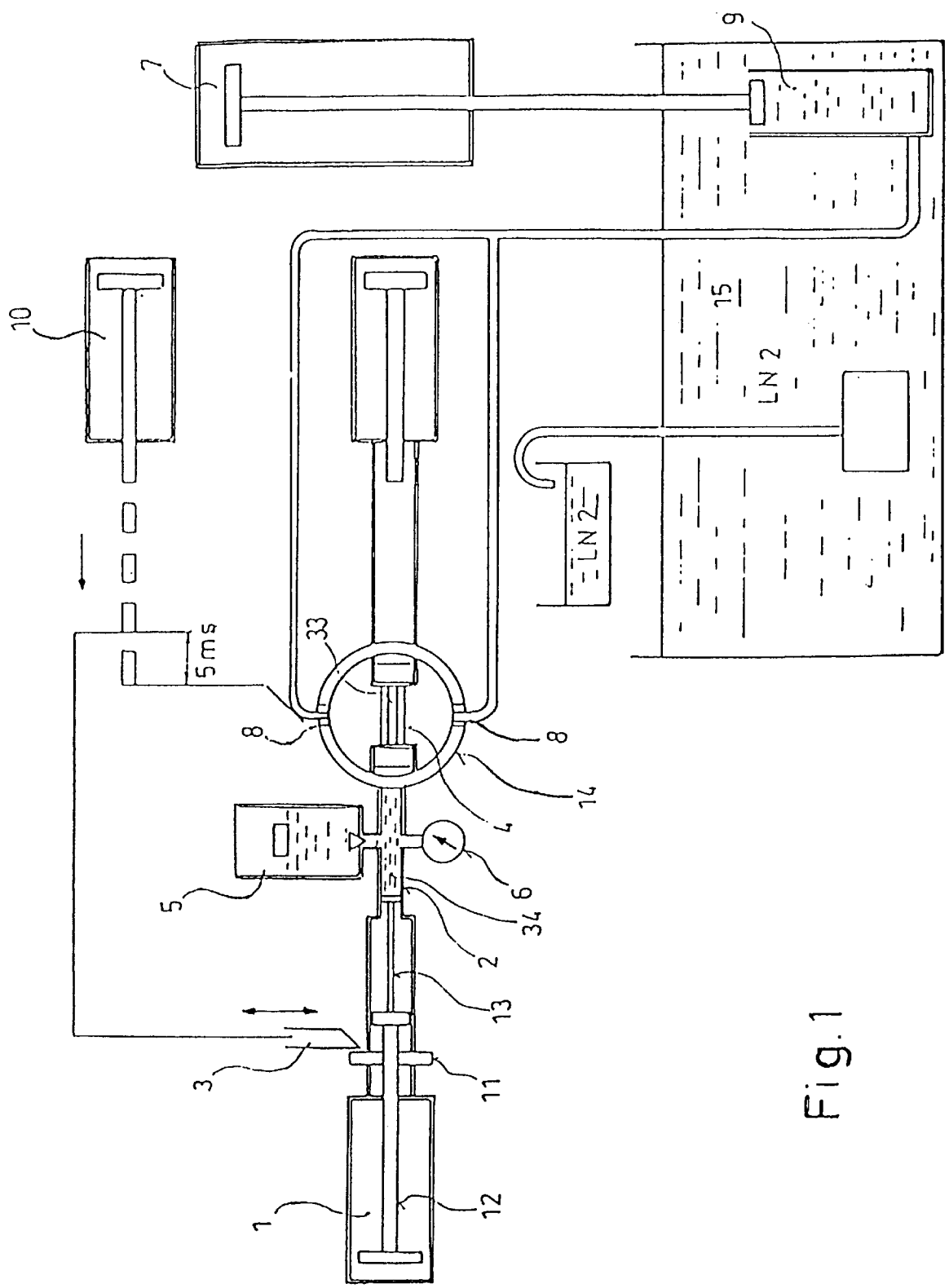
FIG. 1 shows a symbolic drawing of a complete high-pressure freezing system in accordance with the invention.

The exceptional feature of the depicted pneumatic cylinder 1 is the ability to stop the piston by means of the locking device 3. In the locked state, the locking device 3 interacts with a thrust bearing 11. This new arrangement allows a prestressing of the pneumatic cylinder 1 by fully pressurizing the latter in a locked state. After the locking device 3 is released as abruptly as possible, the piston 12 of the pneumatic cylinder accelerates explosively to impinge on a high-pressure piston 13 of a high-pressure cylinder 2.

The high-pressure cylinder 2 comprises a special pressure liquid 34 for building up a pressure exceeding 2000 bar. The pressure liquid 34 does not solidify at low temperatures. It is pressed under pressure onto the sample which is held in a sample holder 4. A practical example of such a liquid is methylcyclohexane as proposed in the European Patent Application EP-A-0853238.

The pressure liquid is topped-up from a refill container 5. A manometer 6 is used to measure the pressure. The sample holder 4 is cooled externally by spraying the cooling medium 15 under pressure from a second pneumatic cylinder 7 via a piston 9 through nozzles 8 against the sample holder 4. In accordance with the invention, the resulting cooling should synchronize exactly with the pressure build-up in the sample holder 4. In the present embodiment, this timing is accomplished by means of a control cylinder 10 which controls the timed sequence of the pressure build-up and the spray cooling.

In accordance with the invention, firstly, the locking device 3 is released abruptly and after a —preferably mechanically — adjustable time interval (ca. 5 ms) the nozzles 8 are opened by means of the annulus gate valve 14 and the cooling medium 15 is simultaneously pressurized by piston 9, propelled by the second pneumatic cylinder 7. The annulus gate valve 14 should be formed such that the area around the nozzles 8 is permanently cooled to prevent as far as possible any heating of the cooling medium 15 prior to its extrusion from the nozzles 8. Liquid nitrogen usually serves as cooling medium 15 although the design is not restricted to its sole use. Other types of cooling media are also possible.

Figure 2:
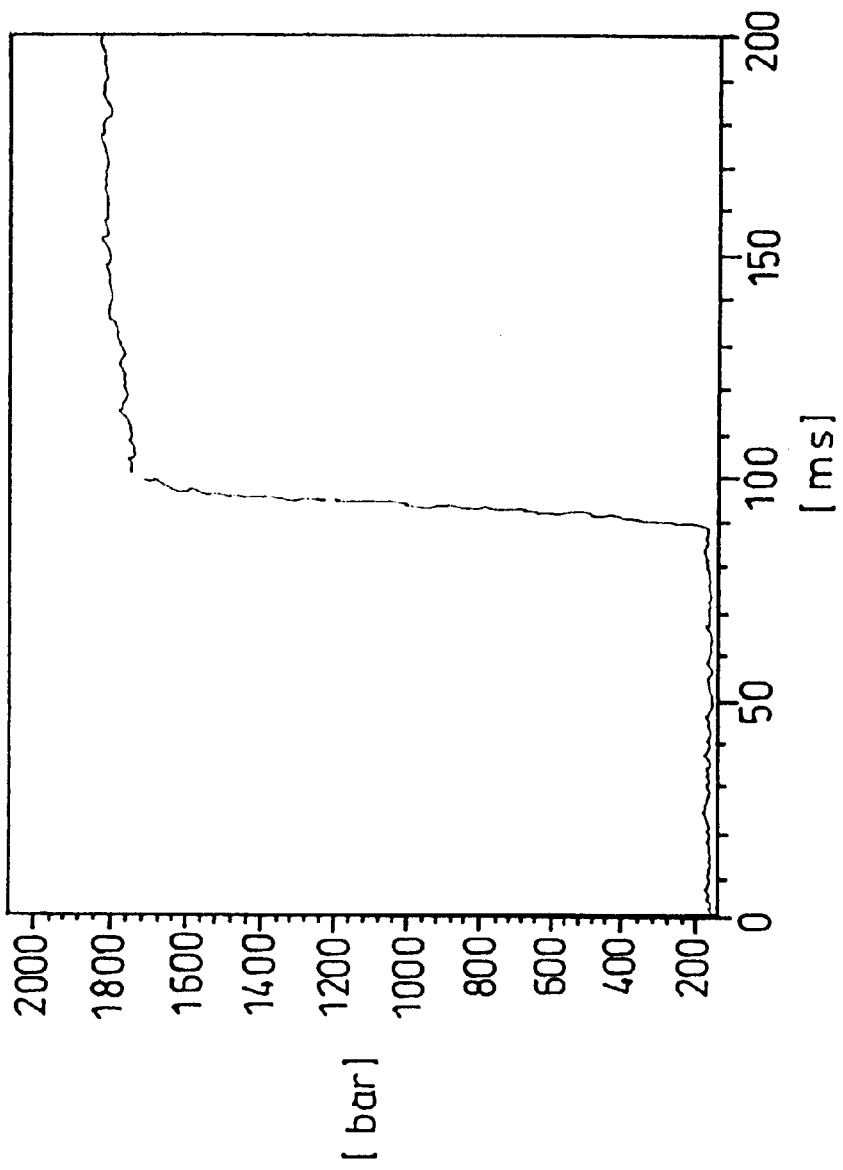
FIG. 2 shows a graph of the course of a high-pressure freezing process for a system in accordance with the invention.

FIG. 2 depicts the preferred pressure rise required for certain samples—and attained for the first time with the arrangement of the present invention.

FIG. 3 illustrates a new type of arm log 16 which accommodates the sample holder 4 and holds it during high-pressure freezing. The sample holder 4 is tubular in order to build up the pressure. In the drawing, the tube 17 is not depicted from end to end as it is very thin. A sample 33 is placed inside the tube. One end of the tube 17 (FIG. 3) is connected to the high-pressure connection of the high-pressure cylinder 2 (FIG. 1) by a conical metal/metal-connection.

The other end of the tube is pressure-sealed by a taper plug 18 (FIG. 4). Consequently, the sample holder 4 is held under tension between the two connections. A spring 19 in the arm log 16 presses the taper plug 18 against the sample holder 4. Attached to the sample holder 4 is a bossed flange 20 with which it is held in the locked state by a spring grab 21, as is shown. On releasing the arm log 16, the spring grab 21 opens allowing the sample holder 4 to drop out. To this end, a pressure head 22 is pushed forwards relative to the housing 23 of the arm log 16 and against the tension of the spring 19. This also results in a relative displacement of the taper plug 18 which is arranged on a rod 24.

Figure 5:
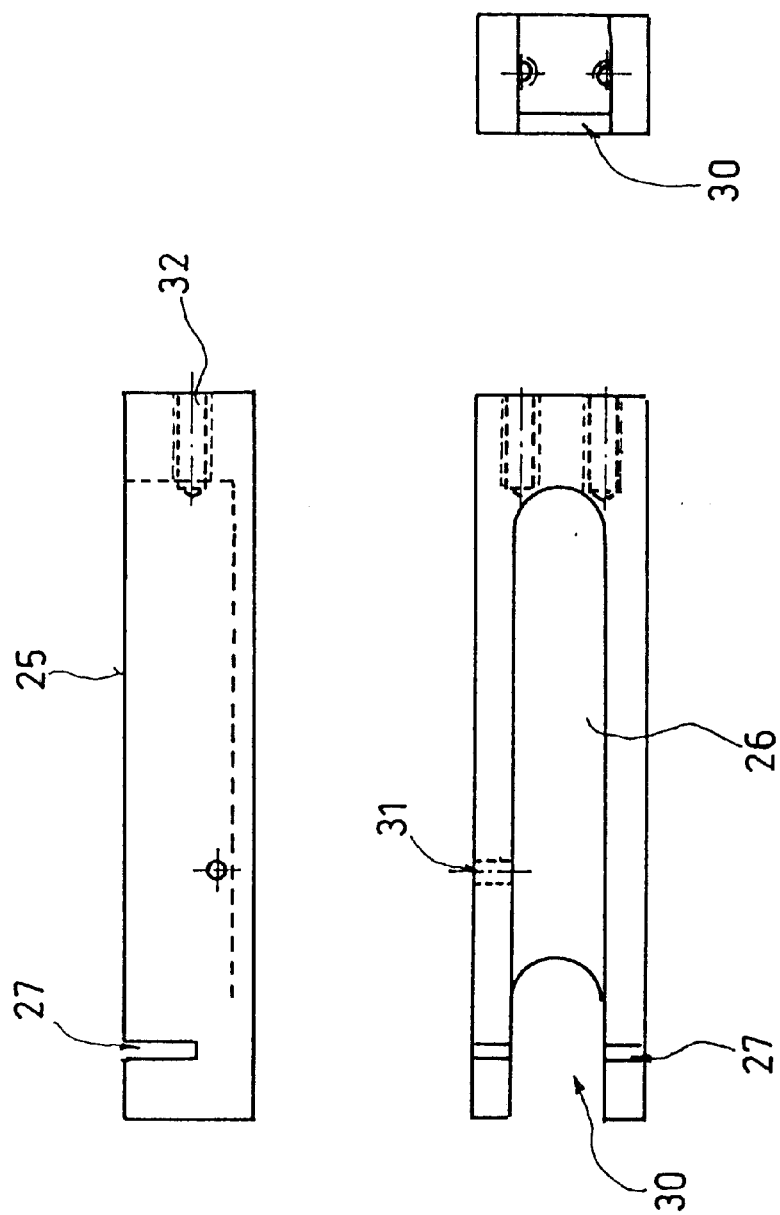
FIG. 5 shows a holder for the arm log holder of FIG. 3 as view, top view and left-hand and right-hand side views.

In practice, this release process occurs after the vitrification of the sample 33. During this process, the arm log 16 is held in a holder 25 in an approximately horizontal position, as illustrated in FIG. 5. The holder 25 has a bed at its disposal 26 which accommodates the arm log 16. The wall of the holder 25 comprises two guide notches 27 which accommodate a bearing axle 28 of the arm log 16. The bearing axle 28 is rigidly connected to the rod 24 and is supported loosely in a longitudinal slot 29 (in the housing 23 of the arm log 16). Thus, the rod 24 can be drawn backwards on the bearing axle 28 relative to the housing 23 to free the other opening of the tube of the sample container 4, which can be effected by the pressure head 22.

Consequently, the present invention allows the sample container to be released from the arm log 16 by one operator with a single movement or by pressing the pressure head. This is simplified further by the arrangement and effect in accordance with the invention, described in the following:

After releasing one end of the tube 17 by the high-pressure connection of the high-pressure cylinder 2, the arm log 16 tilts downwards around the bearing axle 28 as the holder 25 possesses no bottom in the bearing area and thus no support for the arm log 16. After the downward swivel, the operator simply presses the pressure head 22 to release the sample holder 4. This is of particular advantage as the invention shows that a container with liquid cooling medium is positioned beneath the sample holder 4 so that after vitrification, it is possible, within seconds, to immerse or lay the sample holder 4 in the cooling medium in to maintain the cooling temperature.

In accordance with a specific embodiment, all parts in the area around the sample holder 4 and this itself are in addition electrically conductive. It is thus possible by performing a resistance test between the high-pressure cylinder 2 and the holder 25 to measure whether the tube (sample holder 4) is correctly restrained between its two ends. This electrical contact is callipered via a connection 31 on the holder 25. The holder 25 is attached to the device on helical bores 32, which is not described in greater detail.

The invention has been described in detail with particular reference to certain preferred embodiments hereof, but it will be understood that variations and modifications can be effected within the spirit and scope of the invention.

What is claimed is:

1. A high-pressure freezing system to attain an amorphous state during the rapid freezing of aqueous substances, in particular biological samples, the system comprises:
   a cooling device
   a device for pressure build-up which has a drive cylinder with a pressure liquid and a high-pressure cylinder which is driven by the drive cylinder, said high-pressure cylinder impinges the sample with the pressure liquid during high-pressure operation; and
   a prestressing device which has mechanically operated locking device which triggers a rapid pressure build-up in the high-pressure cylinder.

2. The high-pressure freezing system as recited in claim 1 wherein the cooling device comprises at least one nozzle via which, triggered with the pressure build-up in the drive cylinder, a cooling medium is sprayed on the sample.

3. The high-pressure freezing system as recited in claim 2 wherein the cooling liquid is liquid nitrogen.

4. The high-pressure freezing system as recited in claim 1 comprises a control cylinder which is allocated to the drive cylinder.

5. The high-pressure freezing system as recited in claim 4 wherein the control cylinder is allocated to the locking device.

6. The high-pressure freezing system as recited in claim 4 wherein the control cylinder is allocated to the nozzle.

7. The high-pressure freezing system as recited in claim 1 comprises a sample holder, and a holding device for pressing the sample holder against the high-pressure cylinder during high-pressure freezing process to apply the required high pressure.

8. The high-pressure freezing system as recited in claim 7 wherein the holding device comprises an arm log which accommodates the sample holder in a correct position and pressure-sealed on one side during the cooling phase.

9. The high-pressure freezing system as recited in claim 8 wherein the arm log is allocated a holder with a bed to hold the former, from which the arm log can swivel around an axle allowing the sample holder to be swung from a horizontal into a vertical, lower position.

10. The high-pressure freezing system as recited in claim 9 comprises a collecting vessel with cooling medium beneath the holder for depositing the sample holder into the cooling medium after vitrification of a sample.

11. A high-pressure freezing system to attain an amorphous state during the rapid freezing of biological samples, the system comprises:
   a cooling device,
   a device for pressure build-up which has a pneumatic cylinder with a pressure liquid and a high-pressure cylinder which is driven by the pneumatic cylinder, said high-pressure cylinder impinges the sample with the pressure liquid during high-pressure operation and,
   a prestressing device which has a mechanically operated locking device which triggers a rapid pressure build-up in the high-pressure cylinder.

12. The high-pressure freezing system as recited in claim 11 wherein the cooling device comprises at least one nozzle via which, triggered with the pressure build-up in the pressure cylinder, a cooling medium is sprayed on the sample.

13. The high-pressure freezing system as recited in claim 12 wherein the cooling liquid is preferably liquid nitrogen.

14. The high-pressure freezing system as recited in claim 1 comprises a control cylinder which is allocated to the drive cylinder.

15. The high-pressure freezing system as recited in claim 14 wherein the control cylinder is allocated to the locking device.

16. The high-pressure freezing system as recited in claim 14 wherein the control cylinder is allocated to the nozzle.

17. The high-pressure freezing system as recited in claim 14 wherein the control cylinder is a pneumatic cylinder which has a control-time adjusting device.

18. The high-pressure freezing system as recited in claim 17 wherein the pneumatic cylinder is equipped with a pneumatically prestressed pressure component.

19. The high-pressure freezing system as recited in claim 11, comprises a sample holder and a holding device for pressing the sample holder against the high-pressure cylinder during high-pressure freezing process to apply the required high pressure.

20. The high-pressure freezing system as recited in claim 19 wherein the holding device comprises an arm log which accommodates the sample holder in a correct position and pressure-sealed on one side during the cooling phase.

21. The high-pressure freezing system as recited in claim 20 wherein the arm log is allocated a holder with a bed to hold the former, from which the arm log can swivel around an axle allowing the sample holder to be swung from a horizontal into a vertical, lower position.

22. The high-pressure freezing system as recited in claim 21 comprises a collecting vessel with cooling medium beneath the holder for depositing the sample holder into the cooling medium after vitrification of a sample.

23. The high-pressure freezing system as recited in claim 20 wherein the arm log comprises a sping-loaded trip mechanism to clamp and release a sample holder and from which a sample holder can be removed in a single-handed operation.

24. The high-pressure freezing system as recited in claim 11 wherein the cooling device comprises a valve-controlled mechanism for the spraying of the cooling medium and a second pneumatic cylinder which preferably can also be pressurized using initial prestressing force.

\* \* \* \* \*